(12) United States Patent
Pianzola et al.

(10) Patent No.: US 9,155,977 B2
(45) Date of Patent: Oct. 13, 2015

(54) DEVICES FOR THE PRODUCTION OF CYANOPYRIDINES

(71) Applicant: LONZA LTD., Basel (CH)

(72) Inventors: Daniel Pianzola, Brig-Gils (CH); Anton Zenklusen, Baltschieder (CH)

(73) Assignee: LONZA LTD., Basel (CH)

( * ) Notice: Subject to any disclaimer, the term of this patent is extended or adjusted under 35 U.S.C. 154(b) by 0 days.

(21) Appl. No.: 14/165,219

(22) Filed: Jan. 27, 2014

(65) Prior Publication Data

US 2014/0140901 A1    May 22, 2014

Related U.S. Application Data

(62) Division of application No. 12/903,270, filed on Oct. 13, 2010, now Pat. No. 8,680,287.

(60) Provisional application No. 61/252,373, filed on Oct. 16, 2009.

(30) Foreign Application Priority Data

Oct. 16, 2009  (EP) .................................... 09013113

(51) Int. Cl.
*B01D 3/00* (2006.01)
*C07D 213/84* (2006.01)
*C07D 213/85* (2006.01)

(52) U.S. Cl.
CPC .............. *B01D 3/009* (2013.01); *C07D 213/84* (2013.01); *C07D 213/85* (2013.01)

(58) Field of Classification Search
CPC .............................. B01D 3/009; C07D 213/84
See application file for complete search history.

(56) References Cited

U.S. PATENT DOCUMENTS

| 2,861,299 A | 11/1958 | Day |
| 3,929,811 A | 12/1975 | Gelbein et al. |
| 6,118,003 A | 9/2000 | McAteer et al. |
| 2008/0039632 A1 | 2/2008 | Matz et al. |

FOREIGN PATENT DOCUMENTS

| CN | 101045706 | | 10/2007 |
| EP | 0726092 | | 8/1996 |
| GB | 790937 | | 2/1958 |
| WO | 9532055 | A1 | 11/1995 |
| WO | 03022819 | A1 | 3/2003 |
| WO | 2004071657 | A1 | 8/2004 |
| WO | 2005016505 | A2 | 2/2005 |

OTHER PUBLICATIONS

Baiker at al (Appl. Catalysis, 10 (1984), p. 231-241).

*Primary Examiner* — Robert Havlin
(74) *Attorney, Agent, or Firm* — Hoffman & Baron, LLP

(57) ABSTRACT

Subject of the invention is a method for the production of a cyanopyridine, wherein
(A) a gaseous reaction product comprising the cyanopyridine is produced in a reactor,
(B) the gaseous reaction product is quenched with water in a column (2) and a gaseous phase is obtained, which is depleted from at least a portion of the cyanopyridine,
(C) the gaseous phase is transferred to a condenser, in which a condensate is obtained, and the gaseous phase is depleted from at least a portion of the water, and
(D) the gaseous phase from the condenser is passed through at least one heat exchanger.

Another subject of the invention is a device for carrying out the invention.

2 Claims, 1 Drawing Sheet

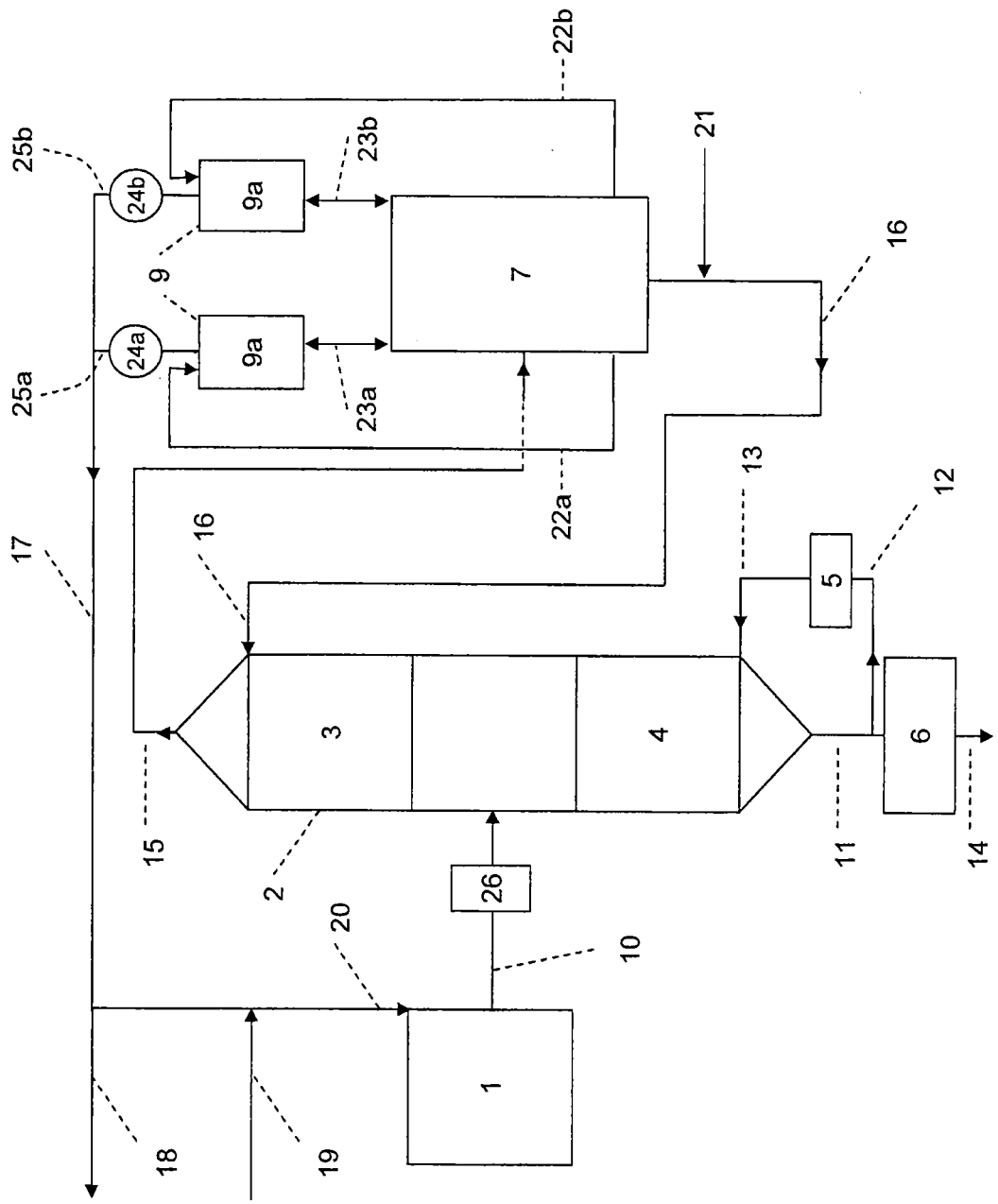

DEVICES FOR THE PRODUCTION OF CYANOPYRIDINES

CROSS REFERENCE TO RELATED APPLICATIONS

This application is based on, and Applicants claim priority from, U.S. patent application bearing Ser. No. 12/903,270, filed Oct. 13, 2010, which claims priority from U.S. Provisional Application bearing Ser. No. 61/252,373, filed Oct. 16, 2009, and European Patent Application bearing Serial No. EP 09013113.7, filed Oct. 16, 2009, all of which are incorporated herein by reference.

The invention relates to methods and devices for the production of cyanopyridines from alkylpyridines.

BACKGROUND OF THE INVENTION

Cyanopyridines are important starting materials for the production of pharmaceutical intermediates and other compounds. 3-methylpyridine (3-picoline) is an intermediate in the industrial production of nicotinic amide and nicotinic acid, which is an essential vitamin of the vitamin B-complex (vitamin $B_3$).

Methods for the production of cyanopyridines from methylpyridines are known in the art. Commonly, the cyanopyridines are oxidized in the presence of a catalyst with ammonia and oxygen. The process is referred to as "ammoxidation" or "oxidative ammonolysis". Various catalysts are known, which comprise specific combinations of catalytic components, which can be coated on carrier materials.

WO 03/022819 discloses methods for the production of heteroaromatic nitriles by ammoxidation of the corresponding alkyl-substituted pyridines. Methods and catalysts for oxidative ammonolysis of alkylpyridines are also disclosed in WO 95/32055.

After the ammoxidation reaction, a gaseous mixture is obtained, which comprises cyanopyridine, ammonia, residual methylpyridines, side products such as pyridine and gases of the reaction stream, such as oxygen, nitrogen, carbon dioxide and water. It is thus necessary to isolate the cyanopyridine from this mixture. Various methods are known in the art to separate the product from the other components.

In the art, methods for isolating the cyanopyridine are known, in which the cyanopyridine is quenched or extracted with an organic solvent.

U.S. Pat. No. 2,861,299 discloses a method for obtaining cyanopyridine from a reaction product, in which the reaction product is passed through a cooling condenser, a dry ice-catcher and a glass wool filter and extracted in a collector using an inert solvent such as benzene. The extraction with benzene as a quenching agent is also disclosed in U.S. Pat. No. 3,929,811. However, the use of organic quenching agents is disadvantageous, because organic solvents such as benzene are relatively expensive, toxic and inflammable at higher temperatures. Further, quenching methods are often complicated and require a large number of process steps.

In order to overcome the problems associated with quenching with organic solvents, methods have been developed in the art in which the use of an organic solvent is not necessary. CN101045706 A discloses a method in which the gaseous product obtained from the ammoxidation reaction is brought into contact with a circulatory aqueous solution in two absorption towers, in order to obtain an aqueous solution of 3-cyanopyridine. Since cyanopyridine is hydrolyzed to nicotinic acid at elevated temperatures and at a high concentration, it is necessary to control the concentration of 3-cyanopyridine in the absorption towers and in the product below 10 wt. %. Further, it is necessary to control the temperature of the circulatory aqueous solution, and thus the temperature in the two absorbent towers, to below 50° C., preferably between 15 and 30° C. When choosing such a low concentration and temperature, more than 95% of the product is recovered. However, the concentration of the product in the final solution is relatively low and it would be desirable to obtain the product at a higher concentration. Further, the loss of 5% cyanopyridine by hydrolysis is still relatively high. The gaseous product, from which cyanopyridine was separated, is not reused in the process and the process requires at least two absorption towers. For reasons of efficiency and also environmental reasons, it would be desirable to make further use of the gaseous product.

In general, the handling of the gaseous phase obtained in the production of cyanopyridines is problematic, because solid deposits tend to accumulate in the devices. Thus especially the reuse of such gaseous phases after depletion of cyanopyridines is problematic. Upon forming of deposits in pipes and other parts of the process plant, the transfer of gases can be reduced. Uniformity of the process cannot be maintained and the efficiency is decreased. The devices have to be cleaned in a time and labour consuming manner, during which the process has to be interrupted.

PROBLEM UNDERLYING THE INVENTION

The problem underlying the invention is to provide a method for the preparation of cyanopyridines, which overcomes the above-mentioned disadvantages.

Specifically, the problem underlying the invention is to provide an improved method for the preparation of cyanopyridines, in which the cyanopyridines are separated from a gaseous mixture in an efficient manner. The process shall be applicable with water as a solvent. The process shall not be affected negatively by deposits in the device. Thus, it shall not, or at least only rarely, be necessary to interrupt the process for removing deposits.

Another problem underlying the invention is to provide a method for the preparation of cyanopyridines, which can be carried out in a closed and circular process. Specifically, at least a portion of the gaseous phase and aqueous phase shall be reused in the process and circulate.

The invention shall provide a relatively simple process and device for the preparation of cyanopyridines from gaseous mixture. The process and the device shall enable the purification of cyanopyridines with a low level of waste products and thus in an environmentally acceptable manner. The cyanopyridines shall be obtained at a high yield. The hydrolysis of the cyanopyridine during the process shall be kept at a low level.

DISCLOSURE OF THE INVENTION

Surprisingly, the problem underlying the invention is solved by the methods and devices according to the claims. Further inventive embodiments are disclosed throughout the description.

Subject of the invention is a method for the production of a cyanopyridine, wherein
   (A) a gaseous reaction product comprising the cyanopyridine is produced in a reactor,
   (B) the gaseous reaction product is quenched with water in a column and a gaseous phase is obtained, which is depleted from at least a portion of the cyanopyridine, (C) the gaseous phase is transferred to a condenser, in which a condensate is obtained, and the gaseous phase is depleted from at least a portion of the water, (D) the gaseous phase from the condenser is passed through at least one heat exchanger.

Without being bound to theory, it is assumed that the problem of solid deposits observed is at least in part related to the formation of a fog during cooling and quenching of a gaseous phase, which contains condensable components. A fog consists of very small droplets of liquid, which result from the condensation and quenching step. Such small droplets can hardly be separated from the gaseous phase by gravitational and inertial forces. Therefore the gaseous stream carries the droplets from the quenching and condensing devices into the subsequent piping and equipments. The droplets consist of condensable components such as water, cyanopyridine, ammonia and others. This is an ideal composition for the formation of nicotine amide and nicotinic acid. If droplets contact the walls of the piping and equipments and the water saturation of the surrounding gaseous phase decreases because of changing temperature and/or pressure, the water will evaporate. As a result, nicotine amide and nicotinic acid, which are not volatile, remain as solid deposits on the walls of the piping and the equipments. Upon forming of deposits in pipes and other parts of the process plant, the transfer of gases can be reduced. Uniformity of the process cannot be maintained and the efficiency is decreased. The devices have to be cleaned in a time and labour consuming manner, during which the process has to be interrupted.

Since the chemical synthesis of nicotine amide and nicotinic acid occurs only in the liquid phase but not in the gaseous phase, the inventive process and device eliminate the fog after the condensing step by heating up the gaseous phase to evaporate the droplets, before the synthesis of nicotine amide and nicotinic acid occurs in significant amounts. As a result, the formation of nicotine amide and nicotinic acid is stopped and the formation of solid deposits is inhibited or at least significantly decreased.

The gas from the condenser is heated in a common heat exchanger A heat exchanger is a device for heat transfer from one medium to another, whereby the media are separated by a solid wall, so that they cannot mix. In the at least one heat exchanger used in step (D) of the invention, the gaseous phase from the condenser is heated up to the temperature 80° C. to 350° C., preferably between 90 and 200° C., more preferably between 100° C. to 130° C. A transition of the wet gaseous phase to a dry gaseous phase occurs within the heat exchanger. During this transition, solid deposits can be formed. Preferably, nicotinic acid and nicotinic amide are deposited and accumulate in the heat exchanger. Preferable a common shell/tube heat exchanger is used, but also any other type of heat exchanger is suitable.

The gaseous phase which leaves the condenser should be transferred to the heat exchanger as soon as possible in order to avoid formation of nicotine amide and nicotinic acid. Preferably, the gaseous phase is transferred from the condenser to the at least one heat exchanger in less than 2 minutes, preferably less than one minute or less than 30 seconds. It is preferred that the connection between the condenser and the at least heat exchanger is as short as possible. Preferably, no devices for treating the gaseous phase are present between the condenser and the heat exchanger. However, control devices, for example for controlling the flow, temperature or pressure, might be present.

Preferably, the temperature of the gas leaving the condenser is at least 50° C., more preferable at least 80° C. lower than the temperature of the gas leaving the heat exchanger Preferably, the temperatures of the condenser and the heat exchanger, are adjusted depending on the pressure. As the skilled person knows, the temperatures for condensing the water in the condenser and for depositing the side products in the heat exchanger may be higher if the pressure is high, and lower if the pressure is low.

In a preferred embodiment of the invention, the amount of the solid deposit, which accumulates in at least one heat exchanger, is monitored. The heat exchanger can be washed, when a predetermined amount of solid has accumulated. Preferably, the amount of deposit in the heat exchanger is monitored by monitoring the pressure. In general, when high levels of deposit accumulate the pressure in front of the heat exchanger increases.

It was found that an efficient removal of the deposits is accomplished by rinsing with water or with an aqueous solution, preferably an aqueous solution obtained during the process. Preferably, the washing solution is an aqueous condensate obtained from the condenser. Preferably, soft water such as distilled water is used. The heat exchanger may be washed when the process is interrupted. Alternatively, the heat exchanger may comprise means for washing, which can be activated whilst the overall process is carried out. Thus the heat exchanger can be washed, whilst the cyanopyridine purification is continued. The washing can be carried out at regular time intervals.

In a preferred embodiment of the invention, in step (D) the gaseous phase is passed through at least two heat exchangers, which are arranged in parallel. In a highly preferred embodiment, two heat exchangers are present which are arranged in parallel. However, also a plurality of heat exchangers may be present, for instance 3, 4, 5 or 6 heat exchangers. When using two or more heat exchangers arranged in parallel, the heat exchangers can be washed alternatively without interrupting the process.

In a preferred embodiment of the invention, whilst washing of at least one heat exchanger, at least one other heat exchanger is not washed. In this embodiment, the overall process can be maintained through at least one heat exchanger. Preferably, each heat exchanger comprises a switch for changing from the operating mode into the washing mode. In the operating mode, the gaseous phase from the condenser is led through the heat exchanger. In the washing mode, the gas stream through the heat exchanger to be washed is interrupted. The washing liquid is preferably reused in the process and may flow back directly into the condenser, quencher or any other part of the plant. In this embodiment of the invention, at least one heat exchanger is always in the operating mode and in use. Thus the interruption of the overall process is not necessary when removing deposits from the heat exchangers. The monitoring, switching and or washing may be carried out automatically or manually.

In a preferred embodiment, a plurality of heat exchangers is present and the heat exchangers are washed at alternating terms. In another embodiment of the invention, a plurality of heat exchangers is present and all the heat exchangers are washed except for one heat exchanger, which is in the operating mode.

The column is preferably an industrial column. However, the inventive process may also be carried out in a laboratory scale. In a preferred embodiment of the invention, the column comprises an absorber section and optionally a stripping section. Absorber columns and stripping columns are common components of industrial chemical process devices. In general, the absorber column or section is for quenching the gaseous reaction product comprising the cyanopyridine in step (B) of the method of the invention. During quenching, at least a portion of the cyanopyridine from the gaseous reaction phase is transferred from the gaseous phase into the aqueous phase.

In a preferred embodiment of the invention, step (B) comprises
  (a) providing a column comprising an absorber section and a stripping section, the absorber section being positioned above the stripping section, such that liquid which passed the absorber section enters the stripping section.
  (b) feeding a gaseous reaction product comprising the cyanopyridine into the column,
  (c) contacting the gaseous phase with an aqueous solution in the absorber section, such that at least a portion of the cyanopyridine is dissolved in the aqueous solution,
  (d) stripping the aqueous solution obtained from the absorber section in step (c) with a stripping gas in the stripping section, and
  (e) eluting the aqueous solution from the bottom of the column.

In a preferred embodiment of the invention, an aqueous solution is introduced on top of the column or near the top of the column, passes the absorber section and, if present, the stripping section and is eluted at the bottom or near the bottom of the column. When passing the column from top to bottom, the aqueous solution has taken up cyanopyridine.

If a stripping section is present below the absorber section, stripping gas which is introduced at the bottom of the column or near the bottom of the column passes the stripping section and the absorber section and is let out at the top of the column or near the top of the column. Thereby a gas stream and a liquid stream can move in the column in opposite directions towards each other.

In one embodiment, the column is a single tower, which has a uniform outer metal wall. In another embodiment, an absorber section and a stripping section are within distinct columns, i.e. an absorber column and a stripping column, both columns being connected, the absorber column being arranged on top of the stripping column, such that both columns together form column. Thus the design and geometry of the column is at the skilled person's discretion, as long as the necessary gas and liquid flow and control of the cyanopyridine absorption and stripping are enabled.

The absorber section is a typical liquid/gas absorber section as known in the art. At the top or above the absorber section, there is an inlet for adding water, preferably pure water. The absorber section comprises devices for letting the aqueous solution flow or drip downwards slowly. Designs and devices are known in the art, which enable good contact between the up flowing gas and the down flowing liquid in the absorber section. Preferably, the absorber section comprises trays or plates, which are known as bubble-cap trays or plates in the art. The column may comprise 2 to 40 or 5 to 20 trays or plates. In general, the more trays are provided, the more cyanopyridine is dissolved. The contact between the gas and the liquid in the absorber section can also be enhanced by other means, for instance packing materials. The packing materials can either be a poored or an ordered package. Ordered packages are preferred, because they are highly efficient especially when the ratio of liquid/gas is low.

In a preferred embodiment of the invention, the temperature in the absorber section is between 40 to 90° C., preferably between 50 and 80° C. The temperature can be achieved without active cooling within the column, when it is the saturation temperature of the gas stream.

In a preferred embodiment of the invention, the gaseous phase is fed into the column in step (b) at a position of the column, which is below the absorber section and above the stripping section. Thus, the gaseous phase can stream upwards into the absorber section to an outlet at or near the top of the column. The gaseous phase does not or not significantly enter the stripping section.

In the stripping section, components are removed from the aqueous solution by a vapour stream. Columns and devices for stripping liquids are known in the art. In a preferred embodiment, the stripping section is a packed or trayed column. The aqueous solution comprising at least a portion of the cyanopyridine, which has passed the absorber section, enters the stripping section. When passing the stripping section and dripping or streaming downwards, the liquid is contacted with a stripping gas. The stripping gas is introduced at the bottom, or near the bottom of the column and below or near the bottom of the stripping section. The stripping section comprises means for enhancing the contact of the liquid phase with the vapor phase. In a preferred embodiment, the stripping section is a trayed tower. In the trays, the liquid flows back and forth horizontally, while the vapor bubbles up through holes and the trays. Thereby, the contact area between the liquid and the vapor phase is enhanced. In another embodiment, or in addition, the stripping section can be a packed column, preferably an ordered package. The stripping section used according to the invention is not limited to these specific embodiments, and any design known in the art is applicable, in which an aqueous solution is stripped from volatile components.

In the stripping section, components from the aqueous cyanopyridine solution, which are more volatile than water, are removed. These are components having a higher partial pressure in aqueous solution compared to their partial pressure in the gas phase. Specifically, ammonia is removed in the stripping section. This is advantageous, because ammonia induces the hydrolysis of cyanopyridine. Further, gaseous components, such as $N_2$, carbon dioxide, hydrogen cyanide, oxygen and aromatic components, such as pyridine and methylpyridines, are removed.

In a preferred embodiment of the invention, the stripping gas is water steam. The stripping of the aqueous solution with water steam is advantageous, because no further gaseous component is introduced into the process and dissolved in the aqueous solution. The water steam can be condensed and become part of the aqueous solution. The water steam can be generated by known means. In a preferred embodiment of the invention, the water steam is obtained from a boiler.

In a preferred embodiment of the invention, the temperature in the stripping section is between 90 and 115° C., preferably between 100 and 110° C. depending on the pressure. Components which have a higher partial pressure in the liquid phase compared to their partial pressure in the gas phase are stripped from the aqueous solution. In a preferred embodiment, the pressure in column is maintained as equal to or slightly above or slightly lower than air pressure. For instance, the pressure may be between 500 and 2000, or between 700 and 1700, or between 900 and 1200 mbar.

The aqueous solution is collected at the bottom of the column. In a preferred embodiment of the invention, the aqueous solution is cooled to a temperature below 50° C., preferably below 40° C. during and/or after the elution (e) by a cooler. The cooling of the aqueous solution is necessary to inhibit the hydrolysis of cyanopyridine.

Since cyanopyridines can be subjected to hydrolysis at high temperatures, the overall time for which the cyanopyridines are kept in column at elevated temperature shall be reduced to a minimum. When the aqueous solution enters the bottom of the column after passing the stripping section, the solution should be eluted from the column as soon as possible. When using the column with the absorber and stripping section as outlined above, it is possible to extract the cyanopyridine from the gaseous reaction product within a relatively short time. For instance, the average time span between feeding the reaction product into the column and eluting the cyanopyridine can be adjusted to less than 1 hour. Although elevated temperatures are applied in the column, the loss of cyanopyridine due to hydrolysis is low, for instance about less than 2 wt %. Preferably, the overall yield of cyanopyridine is above 98%, based on the total cyanopyridine fed into column.

In a preferred embodiment of the invention, the aqueous solution eluted in step (e) comprises more than 15 wt. % cyanopyridine, or preferably more than 25 or more than 30 wt. %. The aqueous solution eluted in step (e) may comprise 15 to 45 w. %, or 25 to 40 wt. % cyanopyridine. Subsequently, the cyanopyridine can be separated from the water by known methods. In a preferred embodiment, the cyanopyridine is extracted, for example with toluene.

In a preferred embodiment of the invention, in the reactor an oxidative ammonolysis of an alkylpyridine is carried out. This reaction comprises a step of contacting the alkylpyridines with a catalyst in the presence of ammonia and oxygen. The method is thus an oxidative ammonolysis (ammoxidation). Usually, oxygen is supplied to the process by air. The gaseous product obtained from an ammoxidation reaction comprises nitrogen (as the main component), carbon dioxide, water vapour, ammonia, oxygen and the product cyanopyridine. Further, unreacted alkylpyridine and pyridine and derivatives thereof as side products are present. Methods for producing cyanopyridines from alkylpyridines by oxidative ammonolysis in the presence of catalysts are known in the art. Such processes are disclosed for instance in WO 03/022819, WO 2005/016505, WO 2004/071657 or EP 0726092 A1. The processes for the production of cyanopyridines from alkylpyridines disclosed therein are incorporated by reference.

After the ammoxidation reaction, the gaseous phase has a high temperature, usually about 300 to 450° C. In an embodiment of the invention, the gaseous phase obtained from the reactor is precooled prior to feeding it into the column in step (b). For instance, the gaseous phase can be cooled to a temperature between approximately 150 and 200° C. The energy gained during precooling can be reused in the overall process. In a preferred embodiment of the invention, the catalyst is provided in a catalyst bed and/or at a temperature in the range of 250 to 450° C., preferably 300 to 390° C. In a preferred embodiment of the invention, the alkylpyridine is contacted with the catalyst in the gaseous phase. In a preferred embodiment of the invention, the alkylpyridine is 3-methylpyridine and thus the cyanopyridine is 3-cyanopyridine. In further embodiments of the invention, the alkylpyridine is 1-methylpyridine and the cyanopyridine is 1-cyanopyridine, or the alkylpyridine is 2-methylpyridine and the cyanopyridine is 2-cyanopyridine. It is also possible to use a mixture of alkylpyridines as starting components. Further, alkylpyridines having two or more alkyl moieties may be used, such as lutidine.

In step (C) of the method of the invention, the gaseous phase, which passed the column, is transferred to a condenser. An aqueous condensate is obtained. Further, organic components with a low vapour point are collected. Preferably, residual cyanopyridine is condensed at this step, if present. The temperature of the condenser is preferably kept at 20-50° C., more preferably 30-40° C.

In a preferred embodiment of the invention, the condensate obtained in step (C) is not discarded. It may be fed into the column, preferably into the absorber section of the column, or may be used for washing the heat exchanger. When refeeding the aqueous condensate into the column, the overall process can be carried out without discarding aqueous solution.

In a preferred embodiment of the invention, at least a portion of the gaseous phase, which passed the at least one heat exchanger in step (D), is fed into the reactor. When refeeding the gaseous phase into the reactor, the overall amount of waste gas can be reduced significantly. However, since during the reaction the reaction gas is depleted of oxygen, a portion of the gaseous phase should be replaced by fresh air, thereby adapting the oxygen level to the necessary level. It was found that this can be achieved by replacing approximately 20% of the gaseous phase by fresh air. In preferred embodiments, approximately 5 to 40 vol. % or 10 to 30 vol. % of the gaseous phase from the heat exchangers is replaced by air, before refeeding it into the reactor.

In a preferred embodiment of the invention, the pressure in the process is adjusted by a compressor or a ventilator. For example, a compressor may be present in the pipe subsequent to the heat exchangers.

In a preferred embodiment of the invention, the process is a closed process, in which the aqueous phase, which is not eluted from the column in step (e), is refluxed, and/or in which at least a portion of the gaseous phase, preferably more than 50 vol. %, is refluxed. According to the invention, a "closed process" means that essentially no gas or liquid is withdrawn or added unless at the positions indicated. In the closed process, water which is eluted in step (e) is replaced. It is preferred that the water is added at the top of the column into the absorber section, but the water could also be added at other positions. Specifically, no waste liquid or only a low amount of waste liquid is discarded. Preferably, the aqueous solution circulates and an aqueous product is obtained at the bottom of the column. The gas pressure may be controlled by valves.

The method of the invention is a method for the production of a cyanopyridine. This means that at least one cyanopyridine is produced. The method is also a method for the production of an aqueous solution of a cyanopyridine, a method for isolation of a cyanopyridine and a method for purification of a cyanopyridine.

Another subject of the invention is a device for the production of a cyanopyridine, comprising
  (i) a reactor for producing a gaseous reaction product comprising a cyanopyridine,
  (ii) a column for quenching the gaseous reaction product with water, such that a gaseous phase is obtained, which is depleted from at least a portion of the cyanopyridine,
  (iii) a condenser for depleting the gaseous phase obtained from the column from at least a portion of the water, in which a condensate is obtained, and
  (iv) at least one heat exchanger, through which the gaseous phase obtained from the condenser is passed.

In a preferred embodiment if the invention, the column comprises
  an absorber section and a stripping section, the absorber section being positioned above the stripping section, such that liquid which passed the absorber section enters the stripping section,
  means for feeding the gaseous reaction product comprising the cyanopyridine into the column,
  the absorber section being adapted for contacting the gaseous phase with an aqueous solution, such that at least a portion of the cyanopyridine is dissolved in the aqueous solution,
  the stripping section being adapted for stripping the aqueous solution obtained from the absorber section with a stripping gas, and means at the bottom of the column for eluting the aqueous solution.

The device of the invention is applicable and adapted for carrying out the method of the invention. Thus the specific embodiments outlined above relating to the method of the invention are applicable in the device of the invention. Another subject of the invention is the use of the device of the invention in a method of the invention. In a preferred embodiment of the invention, the column further comprises means at the top of the column for transferring the gaseous phase, which passed the absorber section, to a condenser, in which an aqueous condensate is obtained.

In a preferred embodiment of the invention, the condenser comprises means for feeding the aqueous condensate from the condenser into the column, preferably the absorber section, and/or means for transferring the gaseous phase, which passed the at least one heat exchanger, into the reactor.

In a preferred embodiment of the invention, the device further comprises a boiler for providing water steam to the stripping section and/or a cooler for cooling the aqueous solution after the elution (e). In a preferred embodiment of the invention, the device further comprises a cyanopyridine. When the device is in use, it comprises a gaseous reaction product in column comprising cyanopyridine and an aqueous solution in column comprising cyanopyridine.

The device comprises means for transporting gases and liquids, such as pipes, with respective inlets and outlets. The pipes, inlets and outlets may comprise controlling means for adjusting and controlling the flow, such as valves and pumps. The gas flow can be adjusted by compressors and ventilators.

The method and the device of the invention solve the above-mentioned problems. The invention provides a simple and efficient process and device for obtaining highly pure aqueous cyanopyridine solutions. The quenching can be carried out with water or an aqueous solution obtained in the process. The use of organic solvents for quenching is not necessary. By the inventive process and device, the problem of undesired deposits of side products throughout the device is overcome. According to the invention, deposits are accumulated in at least one heat exchanger. They can be removed simply by washing with water. When using at least two heat exchangers in parallel, the deposits can be removed without interrupting the overall process. By accumulating the deposits in the heat exchangers, the other components and parts of the device remain free, or essentially free, of such deposits. The inventive method allows the purification of cyanopyridines whilst keeping hydrolysis of cyanopyridines at a low level, for example below 2% or below 1%. The overall process thus can be carried out at a high efficiency and continuity.

FIG. 1 shows a preferred device of the invention. The overall process is adjusted for efficiently removing an aqueous solution of a cyanopyridine from a column (2) whilst a gaseous phase is circulating and solvent is collected in a condenser (7). In FIG. 1, the exemplified column (2) comprises an absorber section (3) and a stripping section (4). Two heat exchangers are included for collecting solid deposits. The device shown is only exemplified and an inventive combination of a condenser and one or more heat exchangers is applicable for any process for the purification of cyanopyridines by quenching with water from a gaseous phase.

The device shown in FIG. 1 comprises a reactor (1), in which a gaseous product comprising the cyanopyridine is obtained and directed to a column (2) through a connection (10). Optionally, the gaseous product is cooled in a cooler (26). The gaseous product is introduced into the column (2) approximately in the middle and between the upper absorber section (3) and the lower stripping section (4). At the bottom of the column, there is a boiler (5), which introduces hot steam near the bottom of the column. At the bottom of the column, there is an outlet and a connection (11) for eluting the aqueous solution comprising cyanopyridine. The solution may pass a cooler (6) and can be isolated for further use through connection (14). At the top of the column (2), there is an outlet and a connection (15) for letting out a gaseous phase depleted of cyanopyridine, which passed the absorber section (3).

The gaseous phase is passed to a condenser (7) through connection (15). The condenser (7) is adjusted for condensing the non-volatile components, i.e. the water and cyanopyridine. The condensed aqueous phase from the condenser (7) is retransferred to the top of column (2) through connection (16). If necessary, a pump supports connection (16). The aqueous condensate is reintroduced at the top, or near the top of the column (2), such that the aqueous phase functions as an absorber liquid in the absorber section. The amount of water, which is eluted together with the cyanopyridine solution, is replaced with fresh water. It can be added anywhere in the process, for instance through a connection (21).

The gaseous phase which passed the condenser (7) is transferred to at least one heat exchanger (9) through connections (23a, 23b). In FIG. 1, two heat exchangers (9a) and (9b) are present, which are arranged in parallel. The gas stream is directed through either or both of the two heat exchangers, depending if the heat exchangers are in the washing or operating mode. By means of switches (24a, 24b) they change from the operating to the washing mode. As the washing liquid, the condensate can be used, which is fed into the heat exchangers through connections (22a, 22b). The washing solution may directly flow back into the condenser through the gas connection (23a, 23b) and is joined with the condensate of the condenser before being transferred into the column (2) through connection (16).

The gaseous phase which passes the heat exchangers (9) can be retransferred into the reactor (1) by connections (17, 20, 25a, 25b). A portion of the waste gas can be discarded through connection (18) and be replaced by fresh air through connection (19).

WORKING EXAMPLE

The inventive process was carried out in an industrial device with the components shown in FIG. 1. In the reactor, cyanopyridine was produced from methylpyridine in an ammoxidation reaction. The components, temperatures, mass flow and pressure in the device were adjusted as shown in table 1 for each compartment. The heat exchangers are switched from the operating to the washing mode by switches (24). The mass flow through the heat exchanger, which is not washed, is adjusted during washing of the other heat exchanger, such that an overall continuous mass flow is maintained. The headline of the table denotes the number of each connection as shown in FIG. 1 and as explained in the corresponding description above. For example, stream No. 14 is the final product stream. The example shows that the invention allows the production of a highly pure cyanopyridine in an efficient continuous process.

TABLE 1

Product streams and conditions according to the working example

| | | Stream No. | | | | | | | | | | | 22a, 22b | 23a, 23b | 25a, 25b |
|---|---|---|---|---|---|---|---|---|---|---|---|---|---|---|---|
| | | 10 | 11 | 13 | 14 | 15 | 16 | 17 | 18 | 19 | 20 | 21 | | | |
| Mass flow | kg/h | 19.630 | 4.229 | 1.010 | 3.219 | 22.506 | 8.095 | 18.110 | 2.935 | 3.338 | 18.513 | 1.899 | 500 ** | 18.112 | 18.112 |
| Temperature | °C. | 350 | 104 | 104 | 40 | 70 | 35 | 35 | 86 | 20 | 160 | 20 | 35 | 35 | 125 |
| Pressure | bar | 1.14 | 1.15 | 1.15 | 1.15 | 1.11 | | 1.10 | 1.00 | | 1.70 | | | 1.10 | 1.05 |
| Components | | | | | | | | | | | | | | | |
| Oxygen | kg/h | 400 | — | — | — | 400 | — | 400 | 65 | 678 | 1.014 | | | 401 | 401 |
| Ammonia | kg/h | 92 | traces | traces | traces | 295 | 203 | 92 | 15 | — | 77 | | | 92 | 92 |
| Water | kg/h | 1.170 | 3.192 | 940 | 2.252 | 4.410 | 8.492 | 617 | 100 | 107 | 625 | 1.699 | | 618 | 618 |
| Methyl-pyridine | kg/h | 19 | traces | traces | traces | 84 | 44 | 19 | 3 | — | 16 | | | 19 | 19 |
| Cyano-pyridine | kg/h | 968 | 1.024 | 70 | 954 | 82 | 55 | 2 | traces | — | 1 | | | 1 | 1 |
| Nitrogen | kg/h | 15.750 | — | — | — | 15.750 | — | 15.750 | 2.553 | 2.552 | 15.750 | | | 15.751 | 15.751 |
| Carbon dioxide | kg/h | 1.096 | traces | traces | traces | 1.375 | 279 | 1.096 | 178 | — | 918 | | | | |
| Hydrogen cyanide | kg/h | 135 | traces | traces | traces | 149 | 15 | 134 | 22 | — | 112 | | | 1.096 | 1.098 |
| Pyridine | kg/h | traces | traces | traces | traces | traces | traces | traces | traces | — | traces | | | traces | traces |
| Nicotinic acid | kg/h | traces | 7 | — | 7 | — | 3 | — | — | — | — | | | — | — |
| Nicotinic acid amide | kg/h | traces | 7 | — | 7 | — | 3 | — | — | — | — | | | — | — |

** kg/wash cycle, condensate of condenser (7)

We claim:

1. A device for the production of a cyanopyridine, comprising:
   (i) a reactor for producing a gaseous reaction product comprising a cyanopyridine,
   (ii) a column for quenching the gaseous reaction product with water, such that a gaseous phase having a temperature of from about 40 to about 90° C. is obtained, which is depleted from at least a portion of the cyanopyridine, wherein the column comprises:
   an absorber section and a stripping section, the absorber section being positioned above the stripping section, such that liquid which passed the absorber section enters the stripping section,
   means for feeding the gaseous reaction product comprising the cyanopyridine into the column,
   the absorber section being adapted for contacting the gaseous phase with an aqueous solution, such that at least a portion of the cyanopyridine is dissolved in the aqueous solution, the stripping section being adapted for stripping the aqueous solution obtained from the absorber section with a stripping gas, and
   means at the bottom of the column for eluting the aqueous solution,
   (iii) a condenser for depleting the gaseous phase obtained from the column from at least a portion of the water, in which a condensate is obtained, wherein the column and the condenser are separate vessels, and
   (iv) at least one heat exchanger, through which the gaseous phase obtained from the condenser is passed and heated.

2. The device of claim 1, wherein the condenser comprises means for feeding the aqueous condensate from the condenser into the absorber section of the column and/or means for transferring the gaseous phase, which passed the at least one heat exchanger into the reactor.

* * * * *